US011056224B1

(12) United States Patent
Fan

(10) Patent No.: US 11,056,224 B1
(45) Date of Patent: Jul. 6, 2021

(54) INTERMITTENT FASTING ASSISTANCE TERMINAL AND METHOD

(71) Applicant: Simple design ltd., Tortola (GB)

(72) Inventor: Ping Fan, Hangzhou (CN)

(73) Assignee: SIMPLE DESIGN LTD., Tortola (GB)

( * ) Notice: Subject to any disclaimer, the term of this patent is extended or adjusted under 35 U.S.C. 154(b) by 0 days.

(21) Appl. No.: 16/845,097

(22) Filed: Apr. 10, 2020

(30) Foreign Application Priority Data

Feb. 24, 2020 (CN) .......................... 202010110761.8

(51) Int. Cl.
| | |
|---|---|
| *G16H 20/60* | (2018.01) |
| *G16H 15/00* | (2018.01) |
| *G06F 3/0483* | (2013.01) |
| *G16H 50/30* | (2018.01) |
| *G06F 3/0482* | (2013.01) |
| *G16H 10/60* | (2018.01) |

(52) U.S. Cl.
CPC .......... *G16H 20/60* (2018.01); *G06F 3/0482* (2013.01); *G06F 3/0483* (2013.01); *G16H 10/60* (2018.01); *G16H 15/00* (2018.01); *G16H 50/30* (2018.01)

(58) Field of Classification Search
CPC ........ G16H 20/60; G16H 10/60; G16H 15/00; G16H 50/30; G06F 3/0482; G06F 3/0483
See application file for complete search history.

(56) References Cited

U.S. PATENT DOCUMENTS

| | | | | |
|---|---|---|---|---|
| 2005/0121504 A1* | 6/2005 | Sanders | ................. | G16H 40/63 235/87 A |
| 2011/0218407 A1* | 9/2011 | Haberman | ............. | G16H 50/20 600/300 |
| 2015/0161355 A1* | 6/2015 | Karra | ..................... | G16H 20/60 705/2 |
| 2017/0103171 A1* | 4/2017 | Sentell | ................... | G16H 10/00 |
| 2018/0240358 A1* | 8/2018 | Crepp | ..................... | G16H 40/67 |
| 2019/0290172 A1* | 9/2019 | Hadad | .................. | A61B 5/0022 |
| 2020/0175886 A1* | 6/2020 | Jain | .......................... | G09B 7/02 |

OTHER PUBLICATIONS

Jen-Hao Hsiao et al., Smart Diet: A Personal Diet Consultant for Health Meal Planning, Oct. 1, 2010, IEEE Xplore, pp. 421-425 (Year: 2010).*

I. Antoniou et al., An Intelligent System for the provision of personalized dietary plans and health monitoring, Jan. 1, 2003, IEEE Xplore, pp. 70-73 (Year: 2003).*

* cited by examiner

*Primary Examiner* — Tam T Tran

(74) *Attorney, Agent, or Firm* — Bayramoglu Law Offices LLC

(57) ABSTRACT

The present invention provides an easy-to-use intermittent fasting assistance terminal and method which integrates recording, guidance and supervision functions. The intermittent fasting assistance terminal is connected to a server through a network, and the intermittent fasting assistance terminal includes an input device, a display device, a processor, and a memory storing an intermittent fasting assistance software program. The processor is configured to execute the intermittent fasting assistance software program, respond to gestures received by the input device and generate corresponding interactive interfaces to be displayed in the display device. The input device is used for inputting user basic data into the intermittent fasting assistance software program and receiving operating gestures of a user to the intermittent fasting assistance software program.

20 Claims, 14 Drawing Sheets

INTERMITTENT FASTING ASSISTANCE TERMINAL AND METHOD

CROSS REFERENCE TO THE RELATED APPLICATIONS

This application is based upon and claims priority to Chinese Patent Application No. 202010110761.8, filed on Feb. 24, 2020, the entire contents of which are incorporated herein by reference.

TECHNICAL FIELD OF THE INVENTION

The present invention relates to the field of mobile communication, in particular to an intermittent fasting assistance terminal and method.

BACKGROUND

Intermittent fasting is not only a weight loss strategy, but also a healthy lifestyle. By promoting your metabolic system to work properly, you can quickly lose weight and improve your health. Intermittent fasting is the oldest diet known to humans, and anyone can use its benefits.

Intermittent fasting usually requires a plan for eating and fasting for a period of time, during which the body will experience many changes and feelings different from usual. When people execute fasting plans on their own schedules alone, it is difficult to make accurate predictions of physical changes and feelings at each stage, and it is easy to give up partway due to concerns, lack of scientific guidance, or reasonable supervision. Therefore, whether for starters or experienced people, if they can obtain a convenient and easy-to-use technology that integrates recording, guidance and supervision functions to assist them in intermittent fasting, it will help successfully complete the fasting plan and enjoy the process.

SUMMARY OF THE INVENTION

The present invention provides an easy-to-use intermittent fasting assistance terminal and method which integrates recording, guidance and supervision functions The Intermittent Fasting Assistance Terminal In one aspect of the invention, provides an intermittent fasting assistance terminal, characterized in that, the terminal is connected to a server through a network, and the terminal includes: an input device, a display device, a processor, and a memory storing an intermittent fasting assistance software program; wherein, the processor is configured to execute the intermittent fasting assistance software program, respond to gestures received by the input device and generate corresponding interactive interfaces to be displayed in the display device;

the input device is used for inputting user basic data into the intermittent fasting assistance software program, and receiving operating gestures of a user to the intermittent fasting assistance software program, including:

receiving a first gesture for selecting a fasting plan,
receiving a second gesture for triggering a start button of the selected fasting plan to enter a third interface; and
receiving a third gesture for ending, aborting, abandoning or fine-tuning the selected fasting plan;

the display device is used for displaying the interactive interfaces of the intermittent fasting assistance software program; the interactive interfaces including:

an initial use start interface for collecting the user basic data;
a first interface for listing intermittent fasting plan options, including a custom plan option, a predefined 24-hour plan option, a predefined multi-day plan option or predefined plan options sorted by fasting levels;
the multi-day plan option referring to, for example, but not limited to, a weekly plan option, a semi-monthly plan option, or a monthly plan option;
a second interface for displaying a start page of the fasting plan selected by the first gesture, the start page including a start button area and a first fasting-period management area; the first fasting-period management area including a current fasting plan schedule and a time adjustment trigger button area; the time adjustment trigger button area associated with a time adjustment page for adjusting a start time of fasting; and
a third interface for displaying a fasting assistance page, including:
a first area, which is a current state indication area, for displaying whether it is currently in a fasting period or not; and if it is currently in the fasting period, further displaying current physiological stage information and a physiological stage information expanding button, the displayed current physiological stage information changing in real time with elapsed time of fasting; and the physiological stage information expanding button is associated with a physiological stage information table and can expand the physiological stage information table after being applied with a gesture.

In a preferred embodiment, as shown in FIG. 2D, FIG. 3A, and FIG. 12, the first area is arranged at the top of the third interface and contains text displaying that it is currently in a fasting or non-fasting period; and when a fasting period is displayed, the current physiological stage information and the physiological stage information expanding button are also displayed, the physiological stage information expanding button associated with the physiological stage information table and can expand the physiological stage information table after being applied with a gesture, as shown in FIG. 3A to FIG. 3B. The physiological stage table includes a plurality of fasting stage pages divided according to the length of the fasting time, as shown in Table 1. The user swipes the page by inputting gestures to the input device to view physiological state information of different fasting stages. The format is shown in FIG. 3B.

As an important function of the terminal and graphical interface system provided by the invention, the first area is designed to directly display the current physiological stage and changes occur to the user in real time, can significantly relieve users' concerns about their physical condition during fasting, reduce anxiety, and increase confidence.

a second area, which is a current progress dynamic display area, displaying information including text or digital information, which contains, in a fasting period, the progress of the current fasting period;
a third area, which is a second fasting-period management area, preferably sharing data, preferably also sharing a format, with the first fasting-period management area, and containing a current fasting plan schedule and a time adjustment trigger button area; and the time adjustment trigger button area associated with a time adjustment page and used for adjusting start times of one or more fasting periods in the selected fasting plan at any time during fasting; and a fourth area, which is a fasting plan quit option area, for ending, aborting, abandoning or fine-tuning the selected fasting plan; and the processor is used for executing the intermittent fasting assistance software program to respond to the gestures received by the input device, display the corresponding interactive interfaces in the display device, and store fasting track data of the user according to a user instruction.

In an alternative embodiment, the current progress dynamic display area, when the selected fasting plan is a predefined plan, the text or digital information further contains, in a fasting period, an end time of the current fasting period.

Preferably, in the current progress dynamic display area, when the selected fasting plan is a predefined plan, the text or digital information further contains, in a fasting period, a number in a percentage format, in order to indicate a degree of completion of the current fasting period.

Preferably, in the current progress dynamic display area, the text or digital information contains, in an eating window, a length of time to the end of the eating window.

In an alternative embodiment, as shown in FIGS. 3A, 4A, 4B and 8B, the current progress dynamic display area further includes a circular progress recording ring, and the text or digital information is displayed in the circular progress recording ring.

In an alternative embodiment, when the selected fasting plan is a predefined plan, as shown in FIGS. 3A, 4A and 4B, a cursor moving along the circular progress recording ring is also displayed, and a part, which has been passed by the cursor, and a part, which has not been reached by the cursor, of the circular progress recording ring are different in color, in order to indicate the degree of completion of the current fasting period. The progress of fasting is displayed in an intuitive and encouraging manner, so that the user is provided with greater confidence to carry on the fasting plan.

In an alternative embodiment, the first fasting-period management area shares data with the second fasting-period management area; and in an alternative embodiment, in the current fasting plan schedule of the first fasting-period management area or the second fasting-period management area, a time unit (such as one-day, 24 hours) in the schedule is represented by a bar-shaped time axis, which consists of a fasting time zone and non-fasting time zone; and the fasting time zone or the non-fasting time zone on each bar-shaped time axis is configured as the time adjustment trigger button area.

In an alternative embodiment, when the selected fasting plan displayed in the second interface is a multi-day fasting plan, the current fasting plan schedule includes bar-shaped time axis arranged in parallel, one day of the selected multi-day fasting plan corresponding to one bar-shaped time axis.

In an alternative embodiment, the interactive interface further includes a fourth interface for displaying save options; and a fifth interface for displaying user data, including basic data and fasting historical data statistics.

In an alternative embodiment, the interactive interfaces further include a first transition interface between the initial use start interface and the first interface: for displaying fasting level options; wherein the input device is used for receiving a first transition gesture before receiving the first gesture for selecting a fasting level to enter the first interface from the interactive interface.

In some of the afore-mentioned alternative embodiments, a normal fasting plan menu option, a graded fasting plan menu option, a fasting knowledge learning menu option, and a user personal data menu option are provided at the bottoms of the first interface and the fifth interface; wherein when the normal fasting plan menu option is chosen, the first interface appears and displays the predefined plan options sorted by the fasting levels;

when the graded fasting plan is chosen, the first transition interface appears and displays fasting level options;

the fasting knowledge learning menu option is associated with stored or online fasting knowledge; and the user personal data menu option is used for accessing user data, including basic data and fasting historical data statistics.

In most alternative embodiments, the terminal may be a touch smart phone or a tablet computer, and the input device and the display device are touch screens.

Intermittent Fasting Assistance Method

In another main aspect of the invention, there is provided an intermittent fasting assistance method, characterized by including: carrying out the following steps by using any terminal described above:

applying a first gesture to an input device to select one fasting plan from intermittent fasting plan options listed in a first interface;

entering a second interface and displaying a start page of the selected fasting plan via a display device;

applying a second gesture to the input device to trigger a start button of the selected fasting plan;

entering a third interface and displaying a fasting assistance page via the display device; and applying a third gesture to the input device to end, abort or abandon the selected fasting plan.

In an alternative method, before the applying the second gesture to the input device, a time adjustment trigger button area is operated in the second interface to adjust a start time of fasting.

In an alternative method, after the applying the second gesture to the input device, the time adjustment trigger button area is operated in the third interface to adjust a start time of fasting.

In an alternative method, after the applying the second gesture to the input device, when the third interface displays that it is during fasting, a physiological stage information expanding button is operated to call out a physiological stage table page to illustrate physiological state changes during different fasting periods.

In an alternative method, after the applying the third gesture to the input device, a fourth gesture is applied to the input device to choose whether to save or delete fasting data which is currently just completed.

Graphical User Interface System in Mobile Terminal Device

In yet another aspect of the present invention, there is provided a graphical user interface system for use in a mobile terminal device, characterized in that the system is used for assisting a user in intermittent fasting, including an initial use start interface for collecting user basic data;

a first interface for listing intermittent fasting plan options, including a custom plan option, a predefined 24-hour plan option, a predefined multi-day plan option or predefined plan options sorted by fasting levels;

a second interface for displaying a start page of a fasting plan selected by the user in the first interface, the start page including a start button area and a first fasting-period management area; the first fasting-period management area including a current fasting plan schedule and a time adjustment trigger button area; the time adjustment trigger button area associated with a time adjustment page for adjusting a start time of fasting; and a third interface for displaying a fasting assistance page entered by triggering, by the user, the start button in the second interface, including:

a first area, which is a current state indication area, for displaying whether it is currently in a fasting period or not; and if it is currently in the fasting period, further displaying current physiological stage information and a physiological stage information expanding button, the displayed current physiological stage information changing in real time with elapsed time of fasting; and the physiological stage information expanding button is associated with a physiological stage information table and can expand the physiological stage information table after being applied with a gesture; a second area, which is a current progress dynamic display area, displaying information including text or digital information which contains, in a fasting period, the progress of the current fasting period;

a third area, which is a second fasting-period management area, preferably sharing data, preferably also sharing a format, with the first fasting-period management area, the second fasting-period management area containing a current fasting plan schedule and a time adjustment trigger button area; and the time adjustment trigger button area associated with a time adjustment page and used for adjusting start times of one or more fasting periods in the selected fasting plan at any time during fasting; and a fourth area, which is a fasting plan quit option area, for ending, aborting, abandoning or fine-tuning the selected fasting plan;

a processor, used for executing an intermittent fasting assistance software program to respond to gestures received by an input device, display corresponding interactive interfaces in a display device, and store fasting track data of the user according to a user instruction.

In an alternative graphical interface system, when the selected fasting plan is a predefined plan, the text or digital information further contains, in a fasting period, an end time of the current fasting period, and a number in a percentage format, in order to indicate a degree of completion of the current fasting period; and the text or digital information contains, in an eating window, a length of time to the end of the eating window.

In an alternative graphical interface system, the second interface further includes a fasting preparing suggestion display area.

In an alternative graphical interface system, the third interface further includes an in-fasting suggestion display area.

In an alternative graphical interface system, the physiological stage information expanding button expands the physiological stage table after being operated by the user, the physiological stage table including a plurality of pages of fasting stages divided in a unit of hours.

In an alternative graphical interface system, the current progress dynamic recording area further includes a circular progress recording ring within which the text information is displayed; and when the selected fasting plan is a predefined plan, a cursor moving along the circular progress recording ring is also displayed, and a part, which has been passed by the cursor, and a part, which has not been reached by the cursor, of the circular progress recording ring are different in color, in order to indicate the degree of completion of the current fasting period.

In an alternative graphical interface system, in the current fasting plan schedules in the first fasting-period management area and the second fasting-period management area, a time unit in the schedules, such as one-day 24 hours, is represented by a bar-shaped time axis, which consist of fasting time zone and non-fasting time zone; and the fasting time zones or non-fasting time zones on each bar-shaped time axis are set as the time adjustment trigger button area.

In conjunction with the previous scheme, when the selected fasting plan displayed in the second interface is the multi-day fasting plan, the current fasting plan schedule includes elongated linear time axes arranged in parallel, one day of the selected multi-day fasting plan corresponding to one bar-shaped time axis.

In an alternative graphical interface system, the system further includes a fourth interface for displaying save options; and a fifth interface for displaying user data, including basic data and data generated during fasting.

In an alternative graphical interface system, the system further includes a first transition interface between the initial use start interface and the first interface: for displaying fasting level options.

In an alternative graphical interface system, a normal fasting plan menu option, a graded fasting plan menu option, a fasting knowledge learning menu option, and a user personal data menu option are provided at the bottoms of the first interface and the fifth interface; wherein when the normal fasting plan menu option is chosen, the first interface appears and displays the predefined plan options sorted by the fasting levels;

when the graded fasting plan is chosen, the first transition interface appears and displays fasting level options;

the fasting knowledge learning menu option is associated with stored or online fasting knowledge; and the user personal data menu option is used for accessing user data, including basic data and data generated during fasting.

The present invention further relates to an intermittent fasting assistance system, characterized by including a server and at least one terminal connected with the server through a network; wherein the server is used for providing an intermittent fasting assistance software program and updated versions thereof which may be downloaded to and installed on the terminal.

According to the above technical schemes, the invention in advantageous in that:

the design of the interactive interfaces comprehensively integrate assistance functions required by intermittent fasting, such as the intuitive and concise encouraging progress tracking page, fasting stage prompts and information of changes in various physiological stages, the time adjustment function and the data storage function; meanwhile, simplicity of the pages is also considered, information in, such as, the time adjustment page, the physiological stage table page, is arranged at a lower layer of the main interface, and is called out via a corresponding button only when it is required by the user. In some preferred embodiments, the current fasting plan schedule and the time adjustment trigger button area are combined into one, as shown in FIGS. 4A and 4B, and in this arrangement, the time adjustment trigger button area is ingeniously hidden in the time axis, thereby simplifying the content displayed in the interface. As time adjustment is not frequently used and needs not to fixedly occupy the display area in the second, especially third, interface, the terminal of the present invention is designed such that these functions not frequently used are not displayed, causing no waste of the display interface, but are also not discarded. During the fasting process, users can focus on more important information, such as fasting process, when to eat, and current physiological state, etc., to complete the fasting and enjoy the process more smoothly and easily.

BRIEF DESCRIPTION OF THE DRAWINGS

In order to more clearly illustrate the technical schemes of the embodiments of the present invention, the drawings to be used in the description of the embodiments are briefly described below, and it is obvious that the drawings in the description below are only some embodiments of the present invention, and that other drawings can be obtained by those skilled in the art without involving any inventive effort.

DETAILED DESCRIPTION OF INVENTION

The embodiments of the present invention will now be described more fully hereinafter with reference to the accompanying drawings, and it is to be understood that the described embodiments are only a few, but not all, embodiments of the invention. Based on the embodiments of the present invention, all other embodiments obtained by those skilled in the art without involving any inventive effort are within the scope of the present invention.

Figure 1:
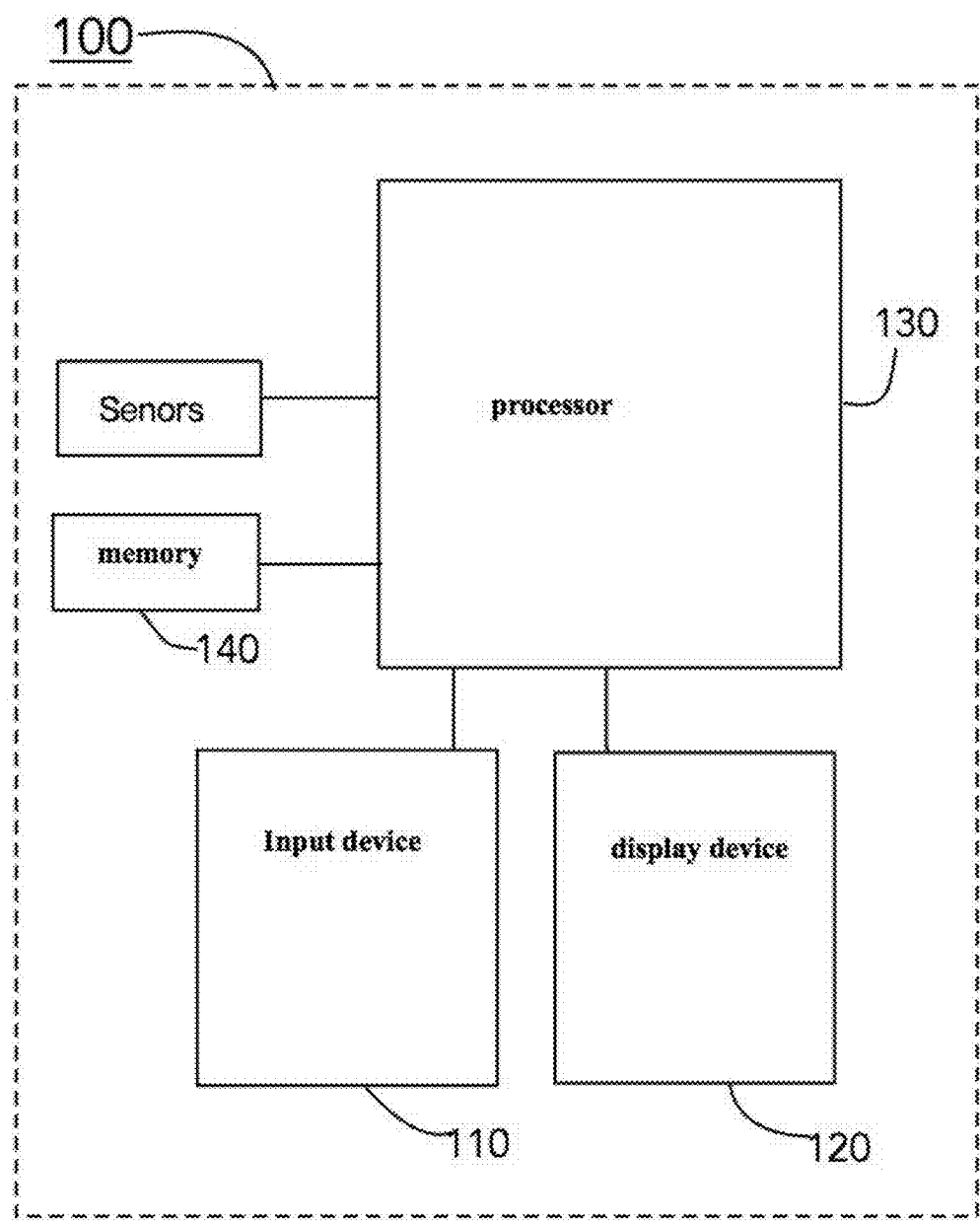
FIG. 1 is a schematic diagram of an intermittent fasting assistance terminal according to the present invention.

Terminal hardware involved in the invention may be a terminal device such as a mobile phone, a tablet computer, a vehicle-mounted computer, etc. It typically includes components such as RF (Radio Frequency) circuitry, a memory, an input device, a display device, sensors, audio circuitry, a WiFi (Wireless Fidelity) module, a processor, and a power supply. Those skilled in the art will realize that the structure of the terminal shown in FIG. 1 is an exemplary embodiment only and is not intended to be limiting of the terminal, and may include more or fewer components than shown, or may combine certain components, or different arrangements of components.

A memory 140 may be used for storing software programs and modules, and a processor 130 executes various functional applications and data processing of the terminal by running the software programs and modules stored in the memory 140. The memory 140 may mainly include a program storage area and a data storage area, wherein the program storage area may store an operating system, an application program required by at least one function (intermittent fasting software program), etc.; and the data storage area may store data created according to use of the terminal (such as fasting data), etc. In addition, the memory 140 may include high-speed random access memory, and may also include non-volatile memory, such as at least one magnetic disk memory device, flash memory device, or other volatile solid state memory device.

A display device 120 may be used for displaying information input by a user, or information and various menus of the terminal provided to the user. The display device 120 may include a display panel. Further, a touch panel may be adopted as the display panel, and when a touch operation on or near the touch panel is detected by the touch panel, the touch operation is transmitted to the processor 130 to determine a type of the touch event, and then the processor 130 provides corresponding visual output to the display panel according to the type of the touch event. In FIG. 1, the input device and the display device are implemented as two separate components to provide the input and display functions of the terminal. However, in most current embodiments, the touch panel and the display panel are integrated to provide the input and display functions of the terminal, for example, the touch panel and the display panel are integrated into a touch screen to provide the input and display functions of the terminal. These are well mature technologies in the art.

Figure 2A:
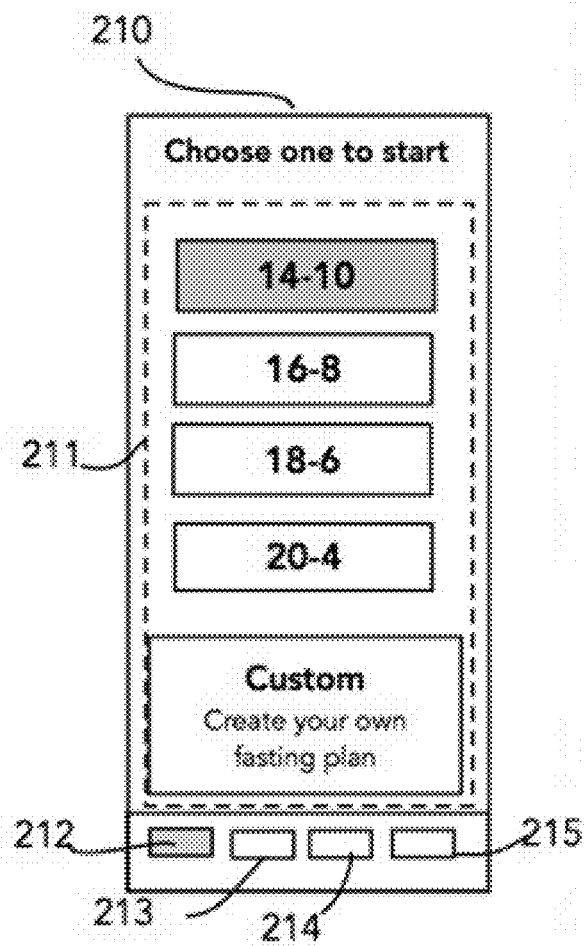
FIG. 2A is a schematic diagram of the first interface.
Figure 2B:
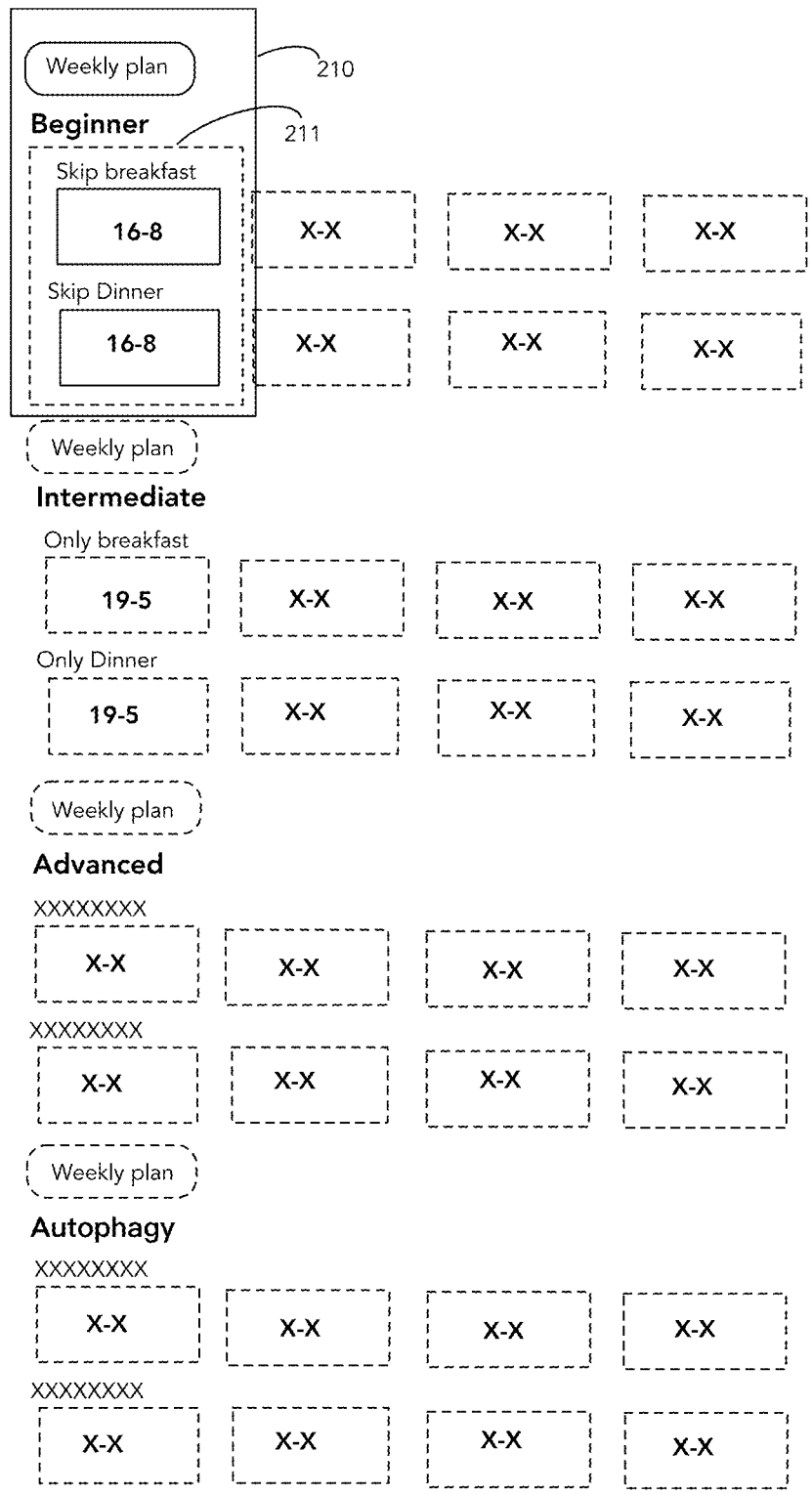
FIG. 2B is a schematic diagram of the first interface, showing predefined program options sorted by fasting levels, wherein other levels and other options may be brought into the interface by gestures.
Figure 2C:
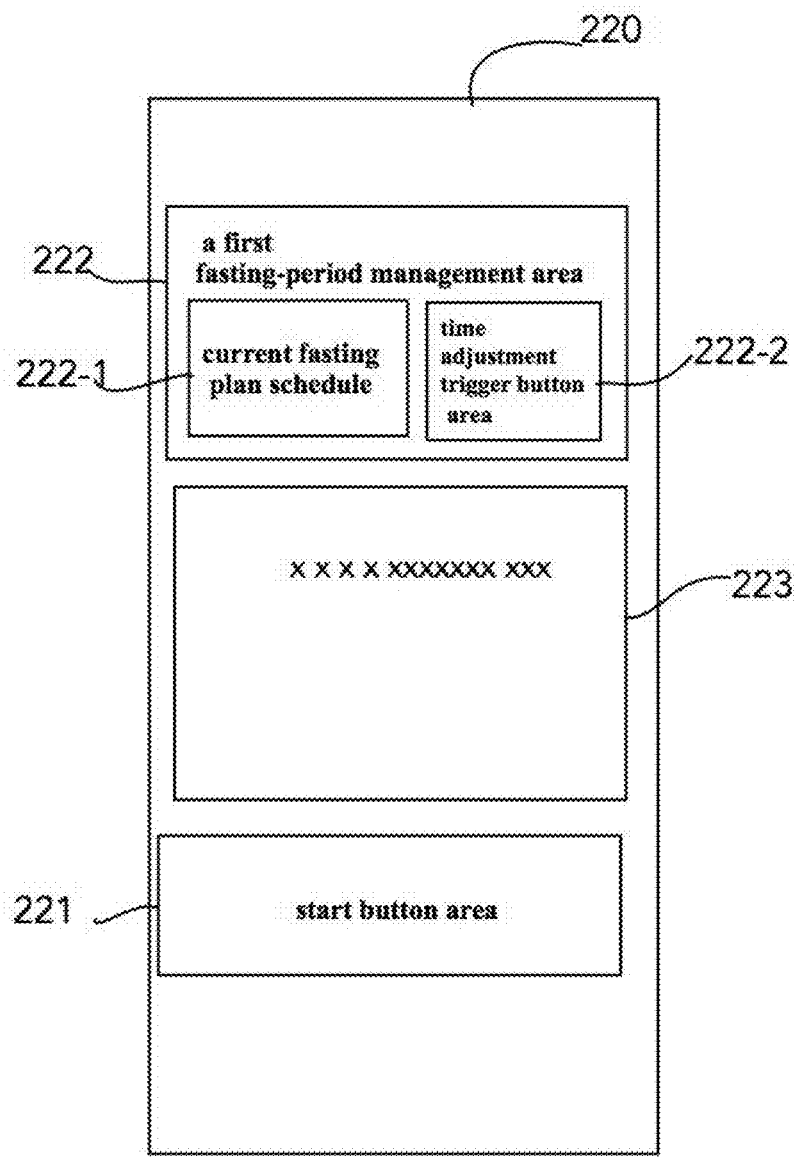
FIG. 2C is a schematic diagram of the second interface.
Figure 2D:
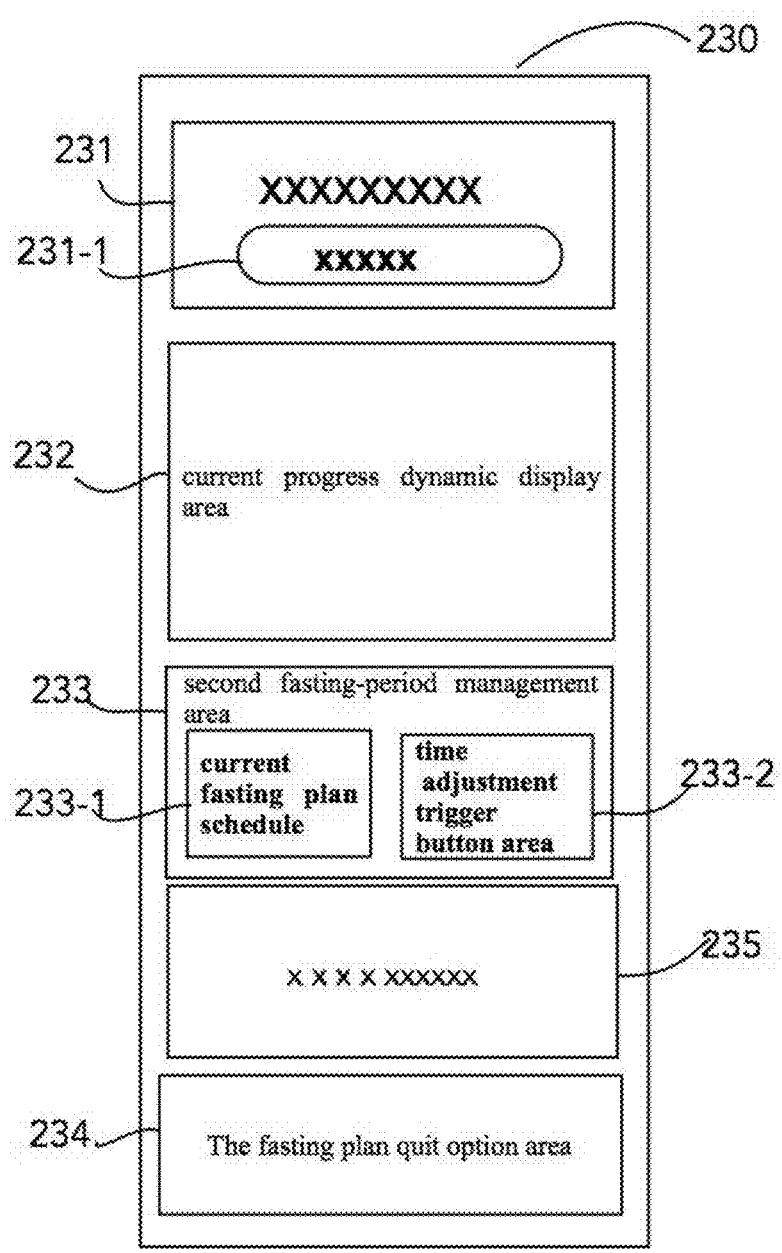
FIG. 2D is a schematic diagram of the third interface.
Figure 3:
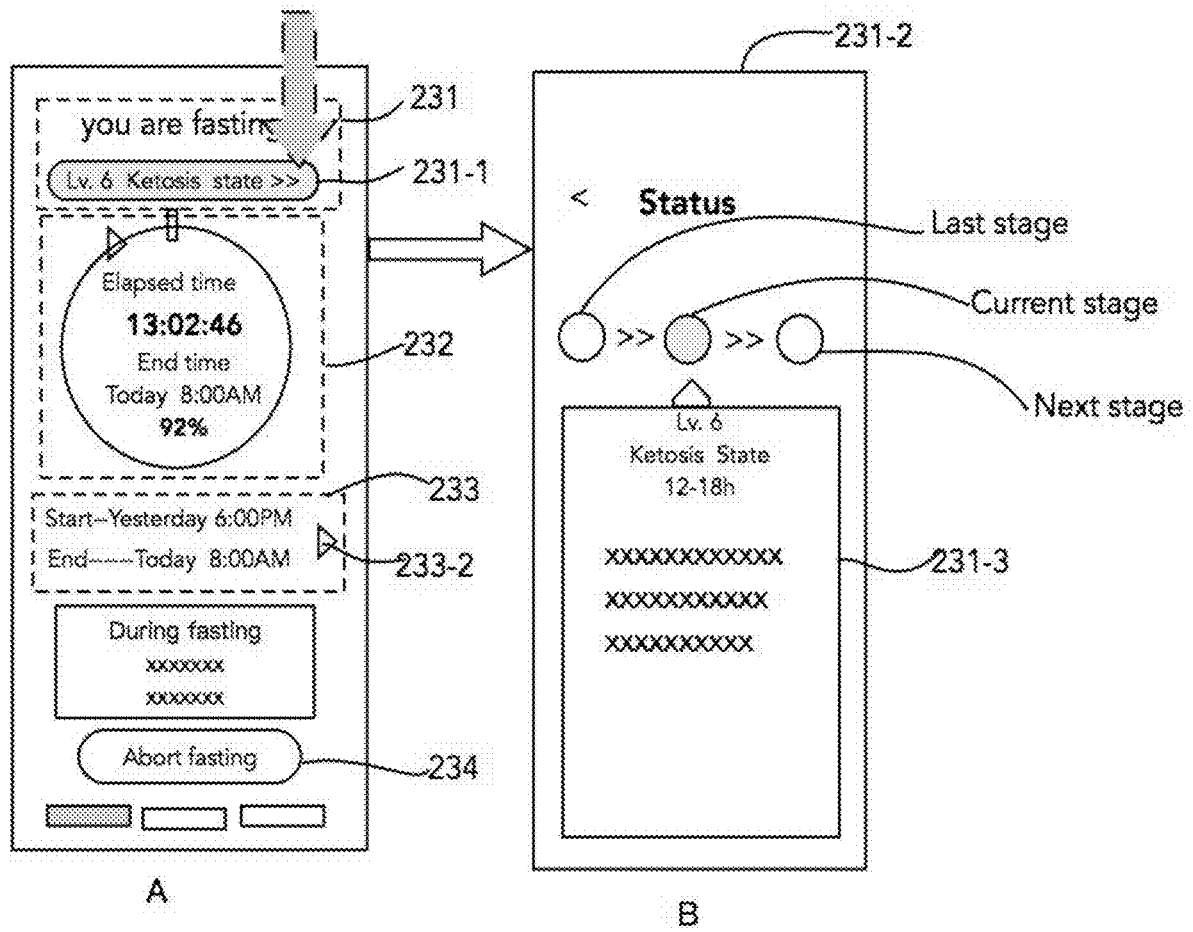
FIG. 3 is a schematic diagram illustrating a physiological stage information expanding button 231-1 in the third interface being operated and switched to a physiological stage table.

The processor 130, which is a control center of the terminal 100, is connected with various parts of the entire terminal via various interfaces and lines, and executes various functions and processes data by running or executing the software programs and/or modules stored in the memory 140 and calling data stored in the memory 140, thereby achieving overall monitoring on the terminal. In an embodiment of the present invention, as shown in FIG. 1, there is provided the intermittent fasting assistance terminal 100, characterized in that, the terminal is connected with a server through a network, and the terminal includes: an input device 110, the display device 120, the processor 130, and the memory 140 storing an intermittent fasting assistance software program; wherein the processor 130 is configured to execute the intermittent fasting assistance software program, respond to gestures received by the input device 110 and generate corresponding interactive interfaces to be displayed in the display device 120;

the input device 110 is used for inputting user basic data into the intermittent fasting assistance software program, and receiving operating gestures of a user to the intermittent fasting assistance software program, including: receiving a first gesture for selecting a fasting plan, receiving a second gesture for triggering a start button; and receiving a third gesture for ending, aborting, abandoning or fine-tuning the selected fasting plan;

the display device 120 is used for displaying all interactive interfaces of the intermittent fasting assistance software program; the interactive interfaces including:

an initial use start interface for collecting user basic data;

a first interface 210 for listing intermittent fasting plan options 211; wherein, as shown in FIG. 2A, a custom plan option, a predefined 24-hour plan option and a predefined multi-day plan option are displayed, or as shown in FIG. 2B, predefined plan options sorted by fasting levels are displayed;

a second interface 220 for displaying a start page of the fasting plan selected by the first gesture, as shown in FIG. 2C, the start page including a start button area 221 and a first fasting-period management area 222; the first fasting-period management area including a current fasting plan schedule 222-1 and a time adjustment trigger button area 222-2; and the time adjustment trigger button area 222-2 associated with a time adjustment table 222-3 for adjusting a start time of fasting; and a third interface 230 for displaying a fasting assistance page, as shown in FIG. 2D, including:

a first area, which is a current state indication area 231, for displaying whether it is currently in a fasting period or not; and if it is currently in the fasting period, further displaying current physiological stage information and a physiological stage information expanding button 231-1, the displayed current physiological stage information changing in real time with elapsed time of fasting; and the physiological stage information expanding button is associated with a physiological stage information table and can expand the physiological stage information table after being applied with a gesture. As shown in FIG. 3B, in the physiological stage information table, a user can slide the screen to view other physiological stage information to view the completed physiological stage and the upcoming physiological changes.

Examples of the information displayed on the physiological stage information expansion button 231-1 at different elapsed fasting time are shown in Table 1 below.

TABLE 1

| Elapsed fasting time | The realtime information displayed on physiological stage information expansion button 231-1 |
| --- | --- |
| 0-2 h | Lv. 1 Blood sugar raises |
| 2-5 h | Lv. 2 Blood sugar falls |
| 5-8 h | Lv. 3 Glycogen Reserve Drops |
| 8-10 h | Lv. 4 Gluconeogensis |
| 10-12 h | Lv. 5 Little Glycogen left |
| 12-18 h | Lv. 6 Ketosis State |
| 18-24 h | Lv. 7 Burn fat |
| 24-48 h | Lv. 8 Autophagy |
| 48-56 h | Lv. 9 Growth hormone goes up |
| 56-72 h | Lv. 10 Sensitive to insulin |
| 72 h | Lv. 11 Immune cells regenerate |

In some preferred embodiment, as shown in FIGS. 2D, 3A, and 12, the first area is arranged at the top of the third interface and contains text displaying that it is currently in a fasting or non-fasting period; and when a fasting period is displayed, the current physiological stage information and the physiological stage information expanding button are also displayed, the physiological stage information expanding button associated with the physiological stage information table and enabling switching to the physiological stage information table after being applied with a gesture, as shown in FIGS. 3A to B; a user can view specific information of the current physiological stage, as well as information of other stages; and as an important function of the terminal and graphical interface system provided by the invention, the first area is designed to directly display the current physiological stage and changes about to occur to the user in real time, so that the user's worries about the physical conditions during fasting can be significantly relieved, reducing the anxiety and nerves, and enhancing the confidence, and the user can complete the fasting plan smoothly and enjoy the benefits to the health brought by fasting;

a second area, which is a current progress dynamic display area 232, displaying information including text or digital information 232-1 which contains, in a fasting period, the progress of the current fasting period;

a third area, which is a second fasting-period management area 233, preferably sharing data, preferably also sharing a format, with the first fasting-period management area 222, the second fasting-period management area containing a current fasting plan schedule 233-1 and a time adjustment trigger button area 233-2; and the time adjustment trigger button area 233-2 associated with a time adjustment table 233-3 and used for adjusting start times of one or more fasting periods in the selected fasting plan at any time during fasting; and a fourth area, which is a fasting plan quit option area 234, for ending, aborting, abandoning or fine-tuning the selected fasting plan.

As shown in FIG. 3A, in some embodiments, in the current progress dynamic recording area 232, when the selected fasting plan is a predefined plan, the text or digital information further contains, in a fasting period, an end time of the current fasting period; and the text or digital information contains, in an eating window, a length of time to the end of the eating window.

In some embodiments, in the current progress dynamic recording area 232, when the selected fasting plan is a predefined plan, the text or digital information further contains, in a fasting period, a number in a percentage format, in order to indicate a degree of completion of the current fasting period.

In an alternative embodiment, as shown in FIGS. 3A, 4A, 4B and 8B, the current progress dynamic recording area 232 further includes a circular progress recording ring within which the text information is displayed.

Figure 4A:
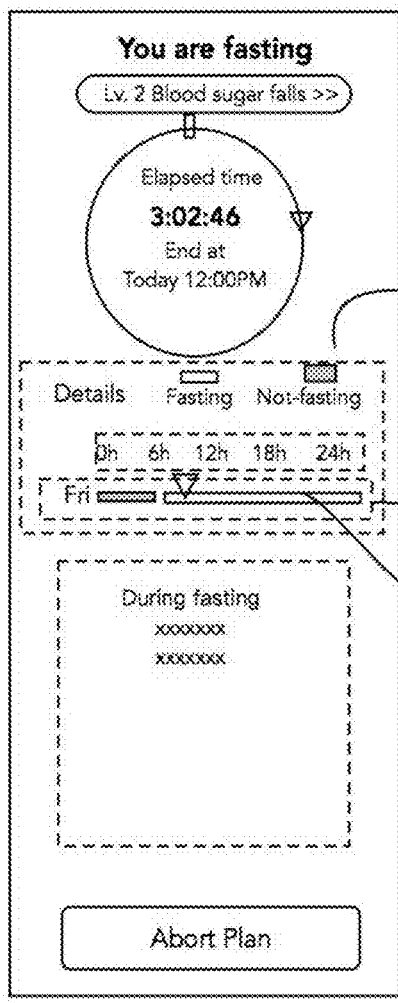
FIGS. 4A-4B are schematic diagrams showing a time display area in the third interface wherein a time unit representing one day is displayed by a bar-shape time axis.
Figure 4B:
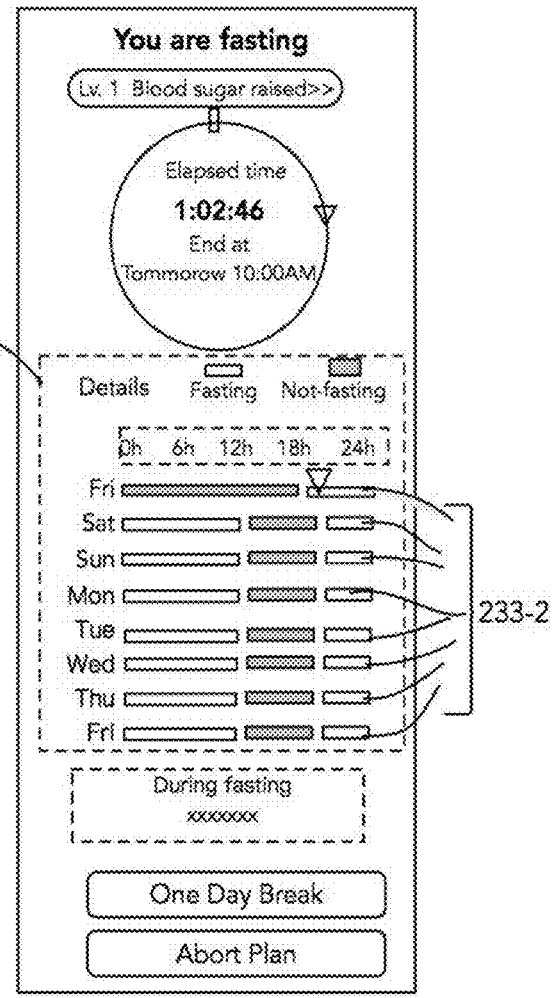

In an alternative embodiment, when the selected fasting plan is a predefined plan, as shown in FIGS. 3A, 4A and 4B, a cursor moving along the circular progress recording ring is also displayed, and a part, which has been passed by the cursor, and a part, which has not been reached by the cursor, of the circular progress recording ring are different in color, in order to indicate the degree of completion of the current fasting period.

The progress of fasting is displayed in an intuitive and encouraging manner, so that the user is provided with greater confidence to carry on the fasting plan.

Preferably, as shown in FIG. 3B, the physiological stage information expanding button 231-1 expands the physiological stage table after being operated by the user, the physiological stage table including a plurality of pages of fasting stages 231-2 divided in a unit of hours with each page of a fasting stage containing text describing physiological information of the stage with more details, and the user slides the pages left and right by applying gestures to the input device to view physiological state information of different fasting stages.

In some embodiments, in the provided terminal, in the current fasting plan schedules 222-1 and 233-1 in the first fasting-period management area 222 of the second interface and the second fasting-period management area 333 of the third interface, one-day 24 hours in the selected fasting plan is represented by a bar-shaped time axis which is composed of fasting time zones and non-fasting time zones; and the fasting time zones or not-fasting time zones on each bar-shaped time axis are set as the time adjustment trigger button area 222-2 or 233-2, as show in FIG. 4A. When the user applies a gesture to the part that has been set as the time adjustment trigger button area, of the bar-shaped time axis, the time adjustment page 222-3 or 233-3 can be called out, as shown in the middle interface diagrams of FIG. 8A or FIG. 8B.

Similarly, when the selected fasting plan displayed in the second interface is the multi-day fasting plan such as a weekly plan, the current fasting plan schedule includes bar-shaped time axis arranged in parallel, one day of the selected multi-day fasting plan corresponding to one bar-shaped time axis.

As shown in FIG. 4B, in the bar-shaped time axis corresponding to each day, the gray indicates the non-fasting time zones and the white indicates the fasting time zones.

In this arrangement, the time adjustment trigger button area is ingeniously hidden in the time axis, thereby simplifying the content displayed in the interface. As time adjustment is not frequently used and needs not to fixedly occupy the display area in the second, especially third, interface, the terminal of the present invention is designed such that these functions not frequently used are not displayed, causing no waste of the display interface, but are also not discarded. During fasting, the user is enabled to better focus on more important information, such as the fasting progress, when to eat, the current physiological state stage, etc., thereby completing the fasting smoothly and happily and enjoying the process.

Figure 5A:
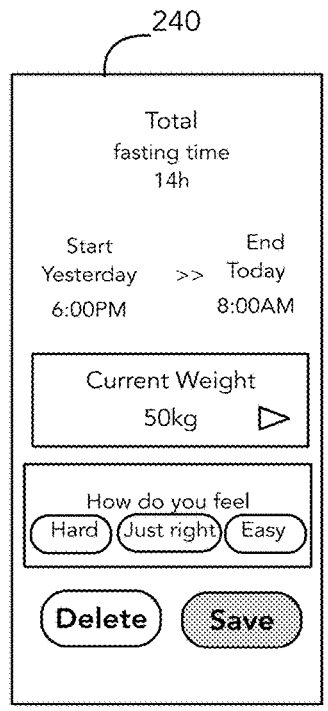
FIGS. 5A-5B illustrate the fourth and fifth interfaces.
Figure 5B:
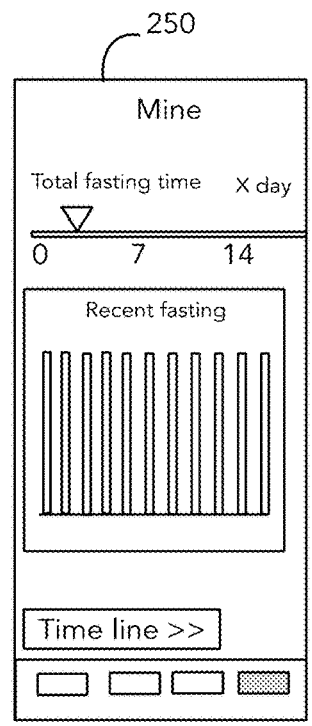

In an embodiment of the terminal according to the invention, the interactive interfaces further include a fourth interface 240, as shown in FIG. 5A, for displaying save options; and a fifth interface 250, as shown in FIG. 5B, for displaying user data, including basic data and fasting historical data statistics.

Figure 6:
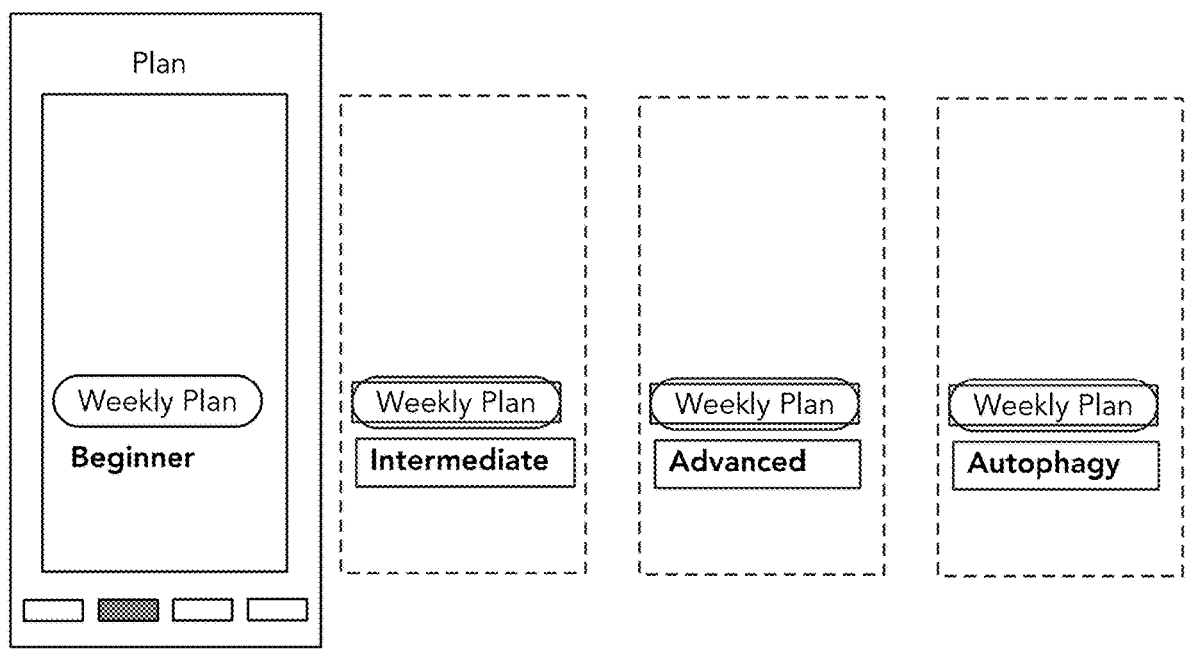
FIG. 6 illustrates the first transition interface.

As shown in FIG. 6, in some embodiments of the terminal of the present invention, in the provided terminal, the interactive interfaces further include a first transition interface between the initial use start interface and the first interface: for displaying fasting level options; wherein the input device is used for receiving a first transition gesture before receiving the first gesture for selecting a fasting level to enter the first interface, as shown in FIG. 2B, from the interactive interface.

In the terminal provided by some embodiments, as shown in FIG. 2A, a normal fasting plan menu option 212, a graded fasting plan menu option 213, a fasting knowledge learning menu option 214, and a user personal data menu option 215 are provided at the bottoms of the first interface and the fifth interface; wherein as shown in FIG. 2A, when the normal fasting plan menu option 212 is chosen, the first interface appears and displays the predefined plan options sorted by the fasting levels;

as shown in FIG. 6, when the graded fasting plan 213 is chosen, the first transition interface appears and displays fasting level options;

the fasting knowledge learning menu option 214 is associated with stored or online fasting knowledge; and the user personal data menu option 215 is used for accessing user data, i.e., the fifth interface 250 shown in FIG. 5B, including user basic data and fasting historical data statistics. In this interface, user authorization options are provided for selecting to synchronize basic health information into a third-party platform database, such as the fit database of the Google account of the user or the health system in the Apple account, so that the user can share the data between different devices.

Figure 7:
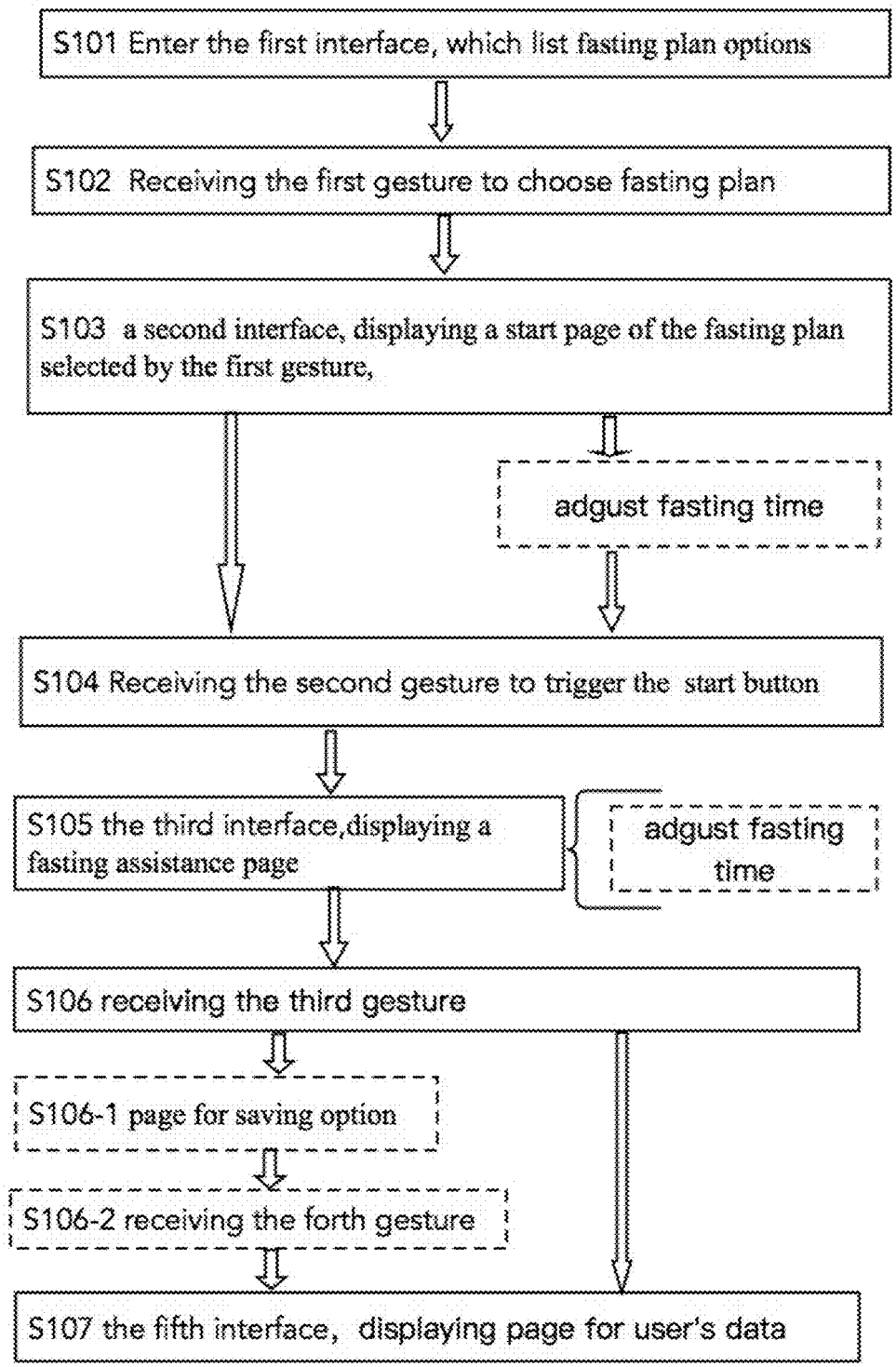
FIG. 7 illustrates an intermittent fasting assistance method according to the present invention.

As shown in FIG. 2C, in the terminal provided by some embodiments, the second interface 220 further includes a fasting preparing suggestion display area 223; and as shown in FIG. 2D, the third interface further includes an in-fasting suggestion display area 235. FIG. 7 illustrates an intermittent fasting assistance method according to the present invention, and the method includes: the following steps are carried out by using any terminal described above:

S101: a display device enters a first interface listing intermittent fasting program options;

S102: an input device receives a first gesture for selecting one fasting plan from the intermittent fasting plan options listed in the first interface;

S103: the display device enters a second interface and displays a start page of the selected fasting plan;

S104: a second gesture is applied to the input device to trigger a start button;

S105: the display device enters a third interface and displays a fasting assistance page;

S106: a third gesture is applied to the input device to end, abort or abandon the selected fasting plan; and S107: the display device enters a fifth interface displaying user data.

Figure 8A:
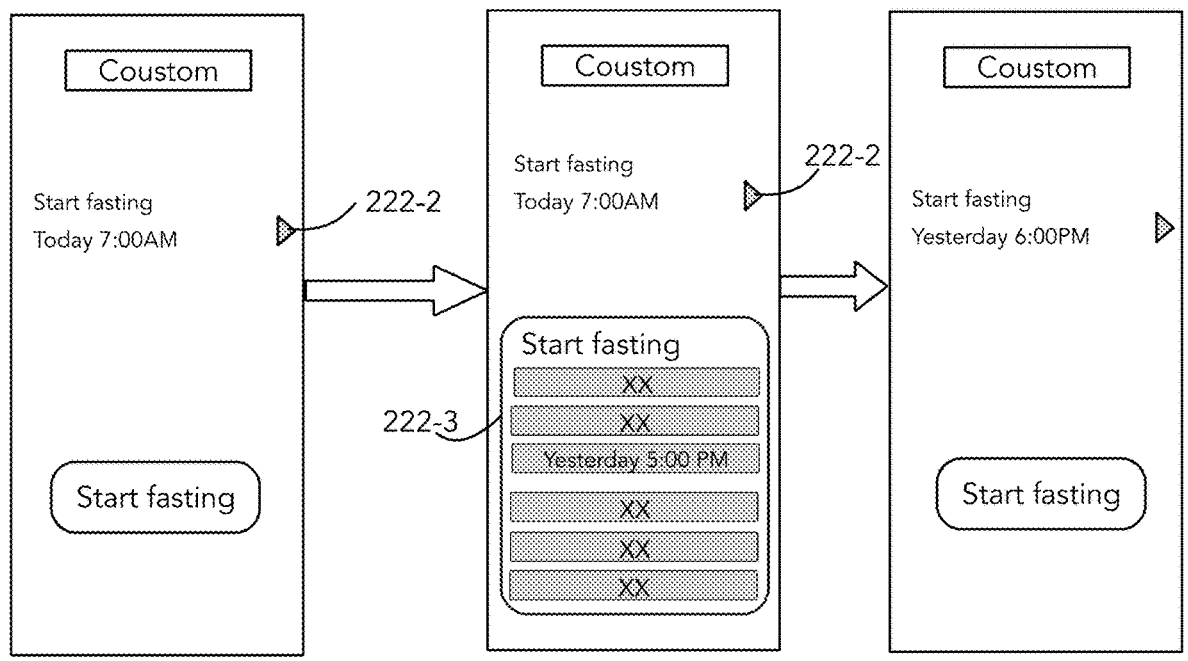
FIGS. 8A-8B are schematic diagrams illustrating different time adjustment modes and corresponding display interfaces in the intermittent fasting assistance terminal, interface and method according to the present invention.

An alternative preferred embodiment is illustrated by a dashed line box in FIG. 7. Between S103 and S104, i.e. before the second gesture is applied to the input device, a time adjustment trigger button area 222-2 is operated in the second interface to adjust a start time of fasting, as illustrated in FIG. 8A.

Figure 8B:
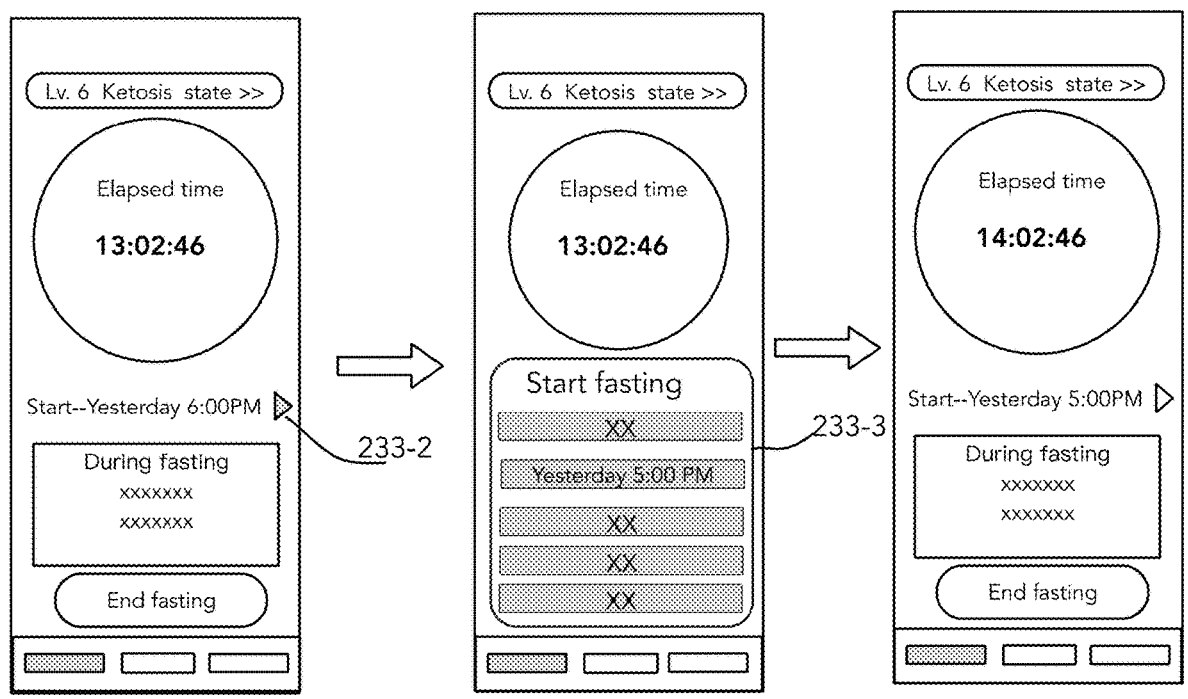

Alternatively, after S104, i.e., after the second gesture is applied to the input device, the time adjustment trigger button area 233-2 is operated in the third interface to adjust a start time of fasting, as illustrated in FIG. 8B.

In all the intermittent fasting assistance methods, it is possible that after the second gesture is applied to the input device, if the third interface displays that it is during fasting, the physiological stage information expanding button 231-1 is operated to call out a physiological stage table page to illustrate physiological state changes during different fasting periods.

After the third gesture is applied to the input device, a save option page S106-1 is entered, and a fourth gesture S106-2 is applied to the input device to choose whether to save or delete fasting data which is currently just completed.

Figure 9:
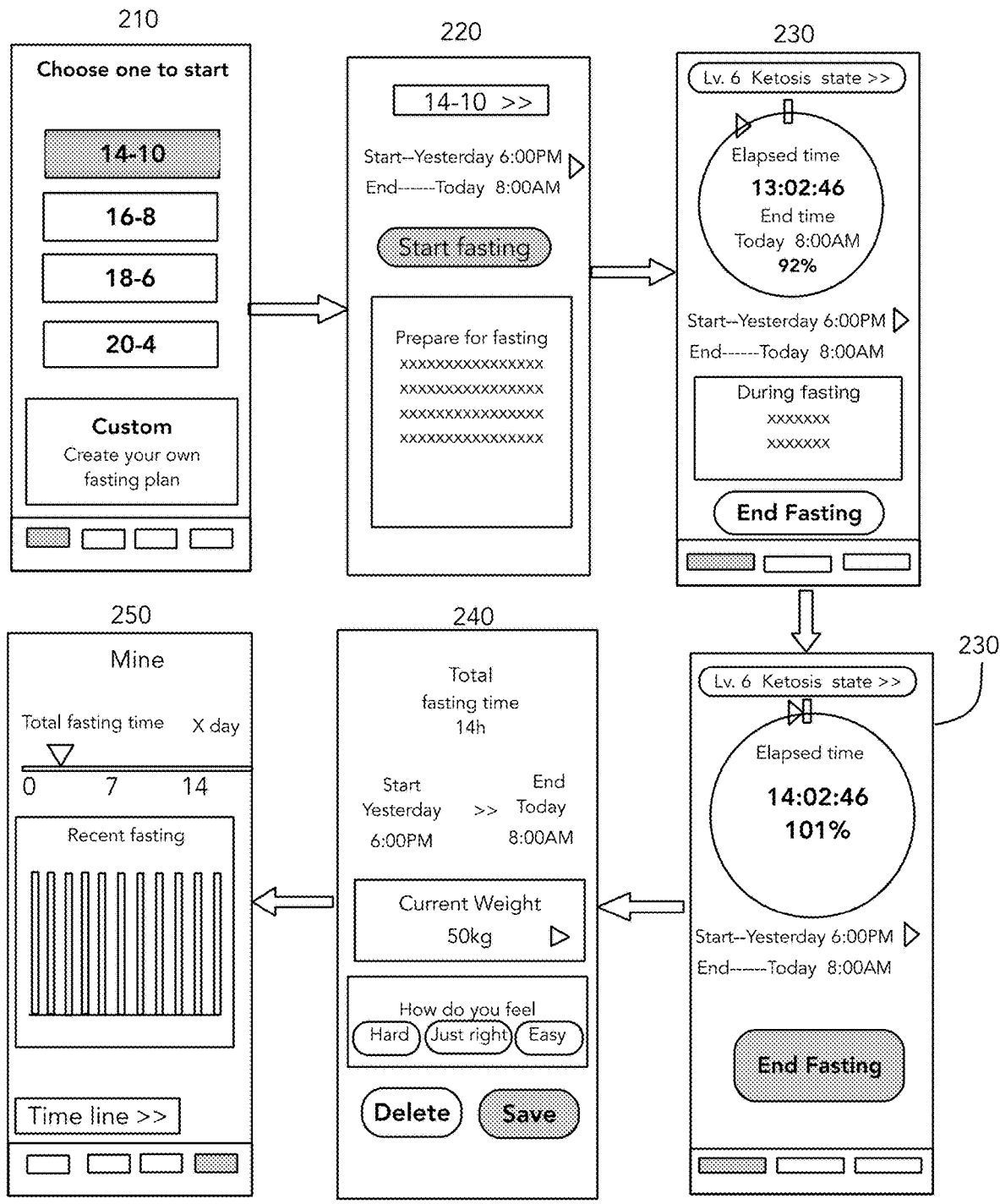
FIG. 9 schematically shows the interfaces entered after the user entering the first interface shown in FIG. 2A and selecting a predefined fasting program option, wherein the gray button indicates areas that has been operated or chosen by a user's gestures.

FIG. 9 schematically shows interfaces entered after the user entering the first interface shown in FIG. 2A and selecting a predefined fasting program option, wherein the gray indicates areas that has been operated or chosen by the user with gestures.

Figure 10:
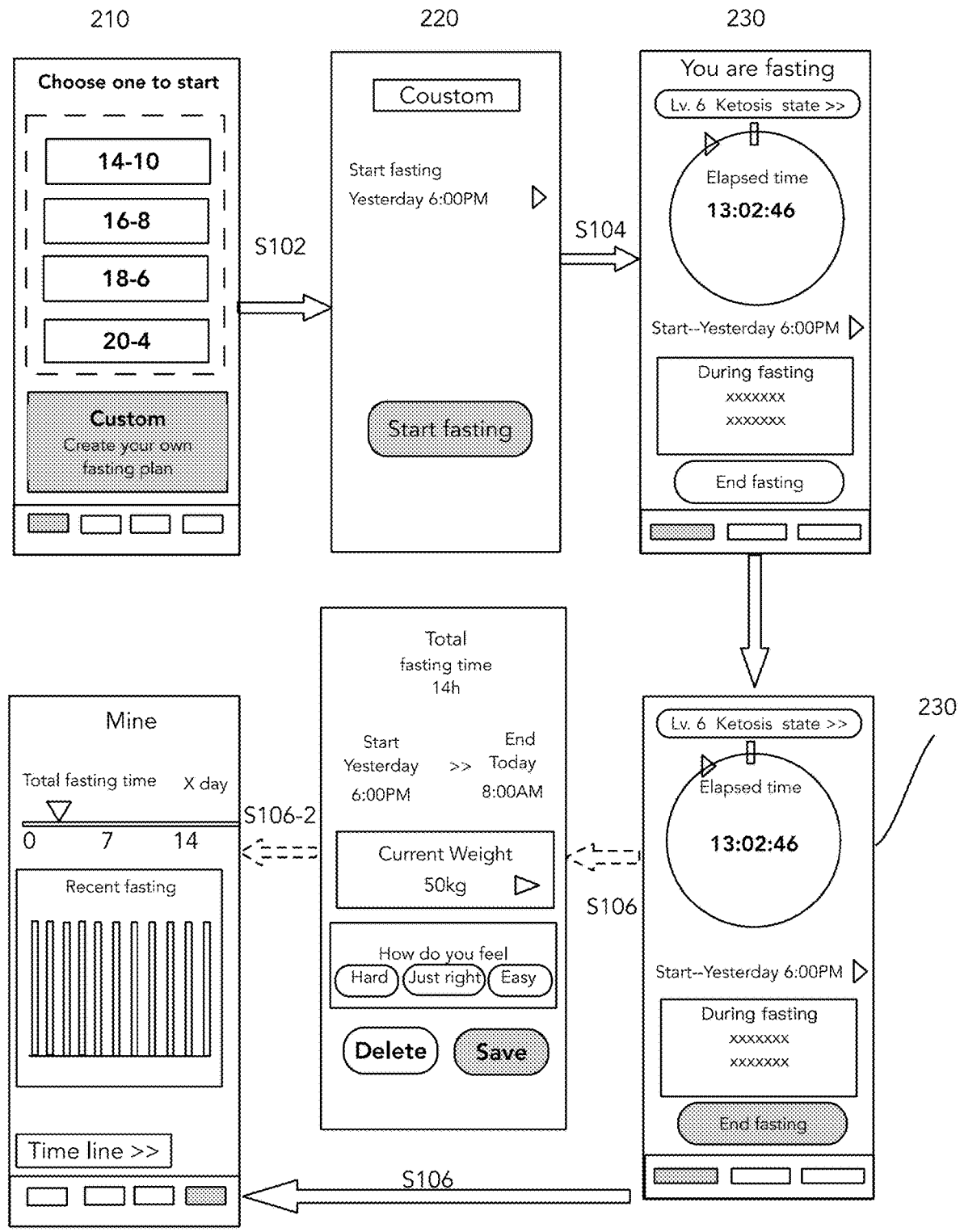
FIG. 10 schematically shows interfaces entered after the user entering the first interface shown in FIG. 2A and selecting a custom fasting plan option, wherein the gray button indicates areas that has been operated or chosen by the user's gestures; dashed lines indicating alternative preferred embodiments.

FIG. 10 schematically shows interfaces entered after the user entering the first interface shown in FIG. 2A and selecting a custom fasting plan option, wherein the gray indicates areas that has been operated or chosen by the user with gestures. Dashed lines indicate alternative preferred embodiments.

Figure 11:
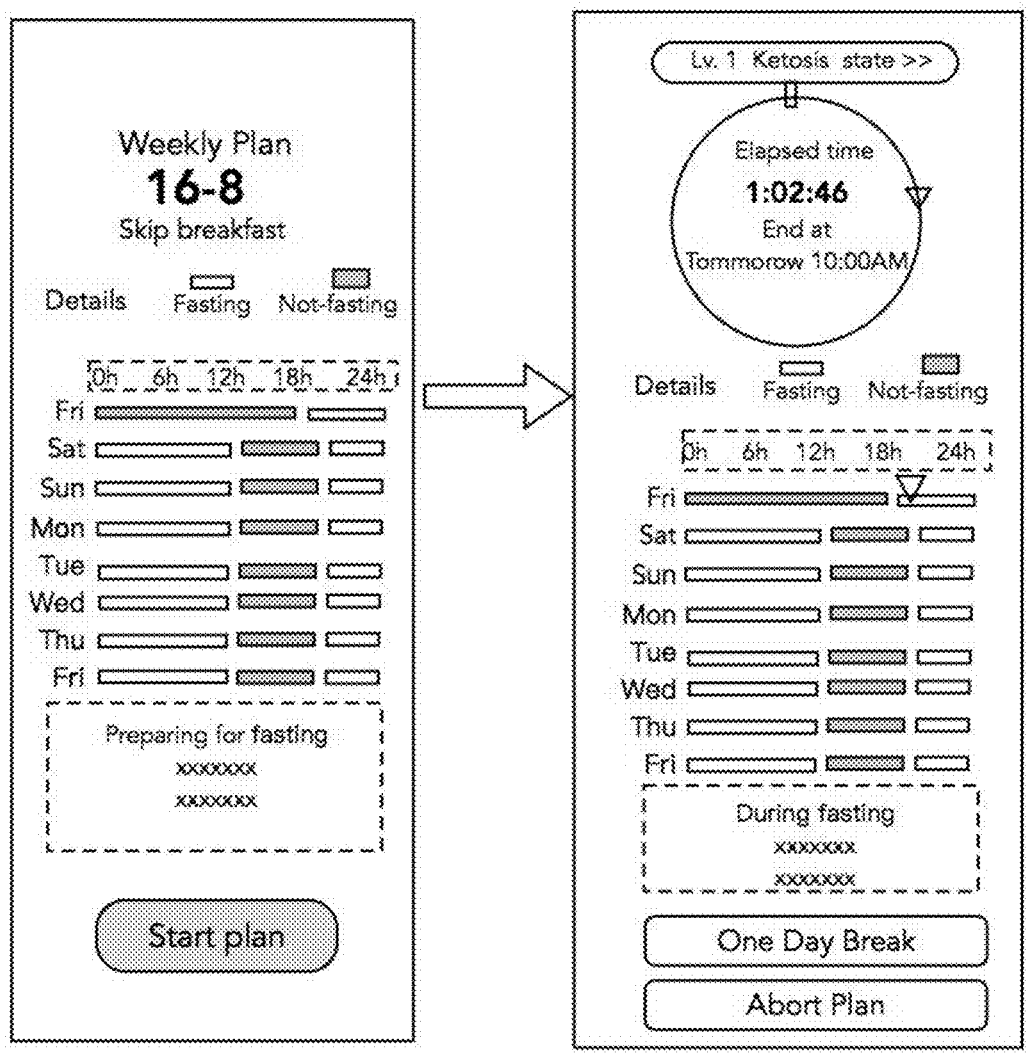
FIG. 11 shows a second interface and a third interface entered after the user entering the first interface shown in FIG. 2B and selecting a predefined fasting weekly plan.

FIG. 11 shows a second interface and a third interface entered after the user entering the first interface shown in FIG. 2B and selecting a predefined fasting weekly plan.

The present invention further provides an intermittent fasting assistance system, characterized by including a server and at least one terminal connected with the server through a network, the terminal being any terminal described above; wherein the server is used for providing an intermittent fasting assistance software program and updated versions thereof which may be downloaded to and installed on the terminal.

Gestures involved in the invention, in most cases, are click gestures, long-press gestures, slide gestures or pinch gestures applied to a touch screen, and may also be gestures applied to physical keys by the user; may be shake gestures applied to the mobile phone by the user; and may be other gestures sensed by sensors, which is not specifically limited in this embodiment.

A fasting period involved in the invention refers to a continuous not-eating period set in a fasting plan, and generally includes settings of a start time and an end time; the fasting period may also refers to a time period between a determined start time and a time when a third gesture (i.e., the end/abort button) is randomly applied by the user. A fasting plan may include one or more fasting periods, such as a one-day fasting plan typically includes one fasting period, while a one-week plan typically includes seven fasting periods.

The eating window involved in the invention refers to an interval between two adjacent fasting periods in a fasting plan, during which free eating is allowed.

Some of the interfaces defined in the present invention, such as the first interface, the second interface, the third interface, the fourth interface, and the fifth interface, can be completely displayed in one screen of the display screen of the display device, while others cannot and also include parts which need to be slide up, down, left or right to be completely displayed.

Those of ordinary skill in the art will appreciate that the elements, algorithms, and method steps described in connection with the embodiments disclosed herein may be implemented as a combination of computer software and electronic hardware. Whether such functionality is implemented as hardware or software depends upon the particular application and design constraints imposed on the particular embodiment. Skilled artisans may implement the described functionality in varying ways for each particular application, but such embodiment decisions should not be interpreted as causing a departure from the scope of the present invention.

What is claimed is:

1. An intermittent fasting assistance terminal, wherein the intermittent fasting assistance terminal is connected to a server through a network, and the intermittent fasting assistance terminal comprises an input device, a display device, a processor, and a memory storing an intermittent fasting assistance software program; wherein,
   the processor is configured to execute the intermittent fasting assistance software program, respond to gestures received by the input device and generate corresponding interactive interfaces to be displayed in the display device;
   the input device is used for inputting user basic data into the intermittent fasting assistance software program, and receiving operating gestures of a user to the intermittent fasting assistance software program, comprising:
   receiving a first gesture for selecting a fasting plan,
   receiving a second gesture for triggering a start button of the fasting plan to enter a third interface; and
   receiving a third gesture for ending, aborting, abandoning or fine-tuning the fasting plan;
   the display device is used for displaying the interactive interfaces of the intermittent fasting assistance software program; the interactive interfaces comprising:
   an initial use start interface for collecting the user basic data;
   a first interface for listing intermittent fasting plan options, comprising a custom plan option, a predefined 24-hour plan option, a predefined multi-day plan option or predefined plan options sorted by fasting levels;
   a second interface for displaying a start page of the fasting plan selected by the first gesture, the start page comprising a start button area and a first fasting-period management area; the first fasting-period management area comprising a current fasting plan schedule and a time adjustment trigger button area; the time adjustment trigger button area associated with a time adjustment page for adjusting a start time of fasting; and
   a third interface for displaying a fasting assistance page, comprising:
   a first area, wherein the first area is a current state indication area, for displaying whether it is currently in a fasting period or not; and if it is currently in the fasting period, further displaying current physiological stage information and a physiological stage information expanding button, the current physiological stage information changing in real time with elapsed time of fasting; and the physiological stage information expanding button is associated with a physiological stage information table and can expand the physiological stage information table after being applied with a gesture,
   a second area, wherein the second area is a current progress dynamic display area, displaying information comprises text or digital information, and the text or digital information contains, in a fasting period, a progress of a current fasting period;
   a third area, wherein the third area is a second fasting-period management area, preferably sharing data, preferably also sharing a format, with the first fasting-period management area, and containing a current fasting plan schedule and a time adjustment trigger button area; and the time adjustment trigger button area associated with a time adjustment page and used for adjusting start times of one or more fasting periods in the fasting plan at any time during fasting; and
   a fourth area, wherein the fourth area is a fasting plan quit option area, for ending, aborting, abandoning or fine-tuning the fasting plan.

2. The intermittent fasting assistance terminal according to claim 1, wherein in the current progress dynamic display area, when the fasting plan is a predefined plan, the text or digital information further contains, in the fasting period, an end time of the current fasting period;
   when the fasting plan is a predefined plan, the text or digital information further contains, in the fasting period, a number in a percentage format, wherein the end time of the current fasting period and the number in the percentage format are configured to indicate a degree of completion of the current fasting period; and in an eating window, the text or digital information contains a length of time to the end of the eating window.

3. The intermittent fasting assistance terminal according to claim 1, wherein the current progress dynamic display area further comprises a circular progress recording ring, and the text or digital information is displayed in the circular progress recording ring;
   when the fasting plan is a predefined plan, a cursor moving along the circular progress recording ring is also displayed, wherein a first part of the circular progress recording ring has been passed by the cursor, and a second part of the circular progress recording ring has not been reached by the cursor, the first part and the second part are different in color to indicate the degree of completion of the current fasting period.

4. The intermittent fasting assistance terminal according to claim 1, wherein the physiological stage table comprises a plurality of fasting stage pages divided according to the elapsed time of fasting, each page represent a fasting stage, the physiological stage table is called out by a gesture applied on the physiological stage information expanding button, and switched to another fasting stage page by an operation gesture.

5. The intermittent fasting assistance terminal according to claim 1, wherein the first fasting-period management area shares data with the second fasting-period management area;
   in the current fasting plan schedule of the first fasting-period management area or the second fasting-period management area, a time unit in current fasting plan schedule is represented by a bar-shaped time axis, consisting of a fasting time zone and non-fasting time zone; and
   the fasting time zone or the non-fasting time zone on each bar-shaped time axis is configured as the time adjustment trigger button area.

6. The intermittent fasting assistance terminal according to claim 5, wherein when the fasting plan displayed in the second interface is a multi-day fasting plan, the current fasting plan schedule comprises bar-shaped time axis arranged in parallel, one day of the multi-day fasting plan corresponding to one bar-shaped time axis.

7. The intermittent fasting assistance terminal according to claim 1, wherein the interactive interface further comprises a fourth interface for displaying save options; and a fifth interface for displaying user data, comprising basic data and fasting historical data statistics.

8. The intermittent fasting assistance terminal according to claim 1, wherein the interactive interface further comprises a first transition interface between the initial use start interface and the first interface; the first transition interface is used for displaying fasting level options; wherein
   the input device is used for receiving a first transition gesture before receiving the first gesture for selecting one of the fasting levels to enter the first interface from the interactive interface.

9. The intermittent fasting assistance terminal according to claim 8, wherein a normal fasting plan menu option, a graded fasting plan menu option, a fasting knowledge learning menu option, and a user personal data menu option are provided at the bottoms of the first interface and the fifth interface; wherein
   when the normal fasting plan menu option is chosen, the first interface appears and displays the predefined plan options sorted by the fasting levels;
   when the graded fasting plan is chosen, the first transition interface appears and displays fasting level options;
   the fasting knowledge learning menu option is associated with stored or online fasting knowledge; and
   the user personal data menu option is used for accessing user data, comprising basic data and fasting historical data statistics.

10. An intermittent fasting assistance method, comprising the following steps
   providing an intermittent fasting assistance terminal, wherein the intermittent fasting assistance terminal is connected to a server through a network, and the intermittent fasting assistance terminal comprises an input device, a display device, a processor, and a memory storing an intermittent fasting assistance software program; wherein,
   the processor is configured to execute the intermittent fasting assistance software program, respond to gestures received by the input device and generate corresponding interactive interfaces to be displayed in the display device;
   the input device is used for inputting user basic data into the intermittent fasting assistance software program, and receiving operating gestures of a user to the intermittent fasting assistance software program, comprising:
   receiving a first gesture for selecting a fasting plan,
   receiving a second gesture for triggering a start button of the fasting plan to enter a third interface; and
   receiving a third gesture for ending, aborting, abandoning or fine-tuning the fasting plan;
   the display device is used for displaying the interactive interfaces of the intermittent fasting assistance software program; the interactive interfaces comprising:
   an initial use start interface for collecting the user basic data;
   a first interface for listing intermittent fasting plan options, comprising a custom plan option, a predefined 24-hour plan option, a predefined multi-day plan option or predefined plan options sorted by fasting levels;
   a second interface for displaying a start page of the fasting plan selected by the first gesture, the start page comprising a start button area and a first fasting-period management area; the first fasting-period management area comprising a current fasting plan schedule and a time adjustment trigger button area; the time adjustment trigger button area associated with a time adjustment page for adjusting a start time of fasting; and
   a third interface for displaying a fasting assistance page, comprising:
      a first area, wherein the first area is a current state indication area, for displaying whether it is currently in a fasting period or not; and if it is currently in the fasting period, further displaying current physiological stage information and a physiological stage information expanding button, the current physiological stage information changing in real time with elapsed time of fasting; and the physiological stage information expanding button is associated with a physiological stage information table and can expand the physiological stage information table after being applied with a gesture,
      a second area, wherein the second area is a current progress dynamic display area, displaying information comprises text or digital information, and the text or digital information contains, in a fasting period, a progress of a current fasting period;
      a third area, wherein the third area is a second fasting-period management area, preferably sharing data, preferably also sharing a format, with the first fasting-period management area, and containing a current fasting plan schedule and a time adjustment trigger button area; and the time adjustment trigger button area associated with a time adjustment page and used for adjusting start times of one or more fasting periods in the fasting plan at any time during fasting; and a fourth area, wherein the fourth area is a fasting plan quit option area, for ending, aborting, abandoning or fine-tuning the fasting plan, the method further comprising applying the first gesture to the input device to select the fasting plan from the intermittent fasting plan options listed in the first interface;

entering the second interface and displaying the start page of the fasting plan via the display device;

applying the second gesture to the input device to trigger the start button of the fasting plan;

entering the third interface and displaying the fasting assistance page via the display device; and applying the third gesture to the input device to end, abort or abandon the fasting plan.

11. The intermittent fasting assistance method according to claim 10, wherein before the applying the second gesture to the input device, the time adjustment trigger button area is operated in the second interface to adjust the start time of fasting.

12. The intermittent fasting assistance method according to claim 10, wherein after applying the second gesture to the input device, the time adjustment trigger button area is operated in the third interface to adjust the start time of fasting.

13. The intermittent fasting assistance method according to claim 10, wherein after applying the second gesture to the input device, when the third interface displays that it is during fasting, the physiological stage information expanding button is operated to call out a physiological stage table page to illustrate physiological state changes during different fasting periods.

14. The intermittent fasting assistance method according to claim 10, wherein after applying the third gesture to the input device, a fourth gesture is applied to the input device to choose whether to save or delete fasting data, wherein the fasting data is currently just completed.

15. A Graphical User Interface system in a mobile terminal device, wherein the system further comprises an initial use start interface for collecting user basic data;

a first interface for listing intermittent fasting plan options, comprising a custom plan option, a predefined 24-hour plan option, a predefined multi-day plan option or predefined plan options sorted by fasting levels;

a second interface for displaying a start page of a fasting plan selected by the user in the first interface, the start page comprising a start button area and a first fasting-period management area; the first fasting-period management area comprising a current fasting plan schedule and a time adjustment trigger button area; the time adjustment trigger button area associated with a time adjustment page for adjusting a start time of fasting; and a third interface for displaying a fasting assistance page entered by triggering, by the user, the start button in the second interface, comprising:

a first area, wherein the first area is a current state indication area, for displaying whether it is currently in a fasting period or not; and if it is currently in the fasting period, further displaying current physiological stage information and a physiological stage information expanding button, the displayed current physiological stage information changing in real time with elapsed time of fasting; and the physiological stage information expanding button is associated with a physiological stage information table and can expand the physiological stage information table after being applied with a gesture;

a second area, wherein the second area is a current progress dynamic display area, displaying information comprising text or digital information, wherein the text or digital information contains, in the fasting period, a progress of a current fasting period;

a third area, wherein the third area is a second fasting-period management area, preferably sharing data, preferably also sharing a format, with the first fasting-period management area, the second fasting-period management area containing a current fasting plan schedule and a time adjustment trigger button area; and the time adjustment trigger button area associated with a time adjustment page and used for adjusting start times of one or more fasting periods in the fasting plan at any time during fasting; and a fourth area, wherein the fourth area is a fasting plan quit option area, for ending, aborting, abandoning or fine-tuning the fasting plan.

16. The Graphical User Interface system according to claim 15, wherein when the fasting plan is a predefined plan, the text or digital information further contains, in the fasting period, an end time of the current fasting period, and a number in a percentage format, wherein the end time of the current fasting period and the number in the percentage format are configured to indicate a degree of completion of the current fasting period; and the text or digital information contains, in an eating window, a length of time to the end of the eating window.

17. The Graphical User Interface system according to claim 15, wherein the second interface further comprises a fasting preparing suggestion display area; and the third interface further comprises an in-fasting suggestion display area, and the physiological stage information expanding button is configured to expand the physiological stage table after being operated by the user, the physiological stage table comprising a plurality of pages of fasting stages divided in a unit of hours.

18. The Graphical User Interface system according to claim 15, wherein the current progress dynamic recording area further comprises a circular progress recording ring, wherein the text or digital information is displayed within the circular progress recording ring; and when the fasting plan is a predefined plan, a cursor moving along the circular progress recording ring is also displayed, wherein a first part of the circular progress recording ring has been passed by the cursor, and a second part of the circular progress recording ring has not been reached by the cursor, the first part and the second part are different in color to indicate the degree of completion of the current fasting period.

19. The Graphical User Interface system according to claim 15, wherein in the current fasting plan schedules in the first fasting-period management area and the second fasting-period management area, a time unit in the fasting plan is represented by a bar-shaped time axis, which consist of fasting time zone and non-fasting time zone; and the fasting time zones or non-fasting time zones on each bar-shaped time axis are set as the time adjustment trigger button area.

20. The Graphical User Interface system according to claim 19, wherein when the fasting plan displayed in the second interface is the multi-day fasting plan, the current fasting plan schedule comprises bar-shaped time axis arranged in parallel, one day of the multi-day fasting plan corresponding to one bar-shaped time axis.

* * * * *